(12) United States Patent
Batich

(10) Patent No.: US 7,390,628 B2
(45) Date of Patent: Jun. 24, 2008

(54) MICROPARTICLE-BASED DIAGNOSTIC METHODS

(75) Inventor: Christopher D. Batich, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 92 days.

(21) Appl. No.: 11/021,026

(22) Filed: Dec. 23, 2004

(65) Prior Publication Data

US 2005/0142063 A1 Jun. 30, 2005

Related U.S. Application Data

(60) Provisional application No. 60/532,167, filed on Dec. 23, 2003.

(51) Int. Cl.
*G01N 33/574* (2006.01)
(52) U.S. Cl. .................. 435/7.23; 435/7.93; 435/325; 436/64; 436/526; 424/9.1
(58) Field of Classification Search ............... 435/7.23, 435/325, 7.1, 7.93; 436/526, 64; 424/9.1
See application file for complete search history.

(56) References Cited

U.S. PATENT DOCUMENTS

| | | | | |
|---|---|---|---|---|
| 4,745,075 | A * | 5/1988 | Hadfield et al. ............. | 436/523 |
| 5,216,130 | A | 6/1993 | Line et al. | |
| 5,340,749 | A * | 8/1994 | Fujiwara et al. ............. | 436/526 |
| 5,646,001 | A * | 7/1997 | Terstappen et al. ......... | 435/7.21 |
| 5,654,006 | A * | 8/1997 | Fernandez et al. .......... | 424/489 |
| 5,919,633 | A | 7/1999 | Tausk et al. | |
| 5,998,588 | A * | 12/1999 | Hoffman et al. ............ | 530/402 |
| 6,221,579 | B1 | 4/2001 | Everhart et al. | |
| 6,268,222 | B1 | 7/2001 | Chandler et al. | |
| 6,327,410 | B1 | 12/2001 | Walt et al. | |
| 6,417,340 | B1 | 7/2002 | Mirkin et al. | |
| 6,495,324 | B1 | 12/2002 | Mirkin et al. | |
| 2002/0012938 | A1* | 1/2002 | Rutenberg et al. .............| 435/6 |

FOREIGN PATENT DOCUMENTS

WO WO 0237944 * 5/2002

OTHER PUBLICATIONS

Dr. Harold Katz New Article Jun. 12, 2002 available online Acid in your mouthwash can be eroding the enamel on your teeth).*
Chang, S. K. et al., 1987, "Detection of Cell Surface Antigens on Biopsied Human Tumor Cells Using Monoclonal Antibody-Containing Fluorescent Microspheres," *Journal of Clinical Laboratory Analysis*, 1(4):326-331.
Database Embase Online, Elsevier Science Publishers, Amsterdam, NL, 1993, Wen, D. Y. et al., "Rapid Detection of Transferrin Receptor Expression in Glioma Cell Lines by Using Magnetic Microspheres," *Neurosurgery*, 1993, US, 33(5):878-881.
Database Biosis Online, Biosciences Information Service, Philadelphia, PA, US, 1986, Homans, A. C. et al., "A Method for the Detection of Multiple Surface Antigens on Small Heterogenous Cell Populations," *American Journal of Clinical Pathology*; 1986; 86(4):469-474.
Database Medline Online, US National Library of Medicine, Bethesda, MD, US; Oct. 2001, Van et al., "Intra-arterial Embolization of Head-And-Neck Cancer With Radioactive Holmium-166 Poly(L-lactic acid) Microspheres: An Experimental Study in Rabbits," *International Journal of Oral Maxillofacial Surgery*, 2001, 30(5):407-413.
Di Paolo, C. et al, 2002, "A Recombinant Immunotoxin Derived From a Humanized Epithelial Cell Adhesion Molecule-Specific Single-Chain Antibody Fragment Has Potent and Selective Antitumor Activity," Clinical Cancer Research, 9(7):2837-2848.
Mashberg, A. et al., 1995, "Early Diagnosis of Asymptomatic Oral and Oropharyngeal Squamous Cancers," A Cancer Journal For Clinicians, 45(6):328-351.
He, X. et al., "A Novel Fluorescent Label Based on Organic Dye-Doped Silica Nanoparticles for HepG Liver Cancer Cell Recognition," *J. Nanosci. Nanotechnol.*, 2004, 4(6):585-9.
Santra, S. et al., "Conjugation of Biomolecules with Luminophore-Doped Silica Nanoparticles for Photostable Biomarkers," *Anal. Chem.*, 2001, 73(20):4988-4993.
Santra, S. et al., "Development of Novel Dye-Doped Silica Nanoparticles for Biomarker Application," *J. Biomed. Opt.*, 2001, 6(2):160-6.
Santra, S. et al., "Luminescent Nanoparticle Probes for Bioimaging," *J. Nanosci. Nanotechnol.*, 2004, 4(6):590-9.
Santra, S. et al., "TAT Conjugated, FITC Doped Silica Nanoparticles for Bioimaging Applications," *Chem. Commun. (Camb)*, 2004, 24:2810-1.
Tapec, R. et al., "Development of Organic Dye-Doped Silica Nanoparticles for Bioanalysis and Biosensors," *J. Nanosci. Nanotechnol.*, 2002, 2(3-4):405-9.
Zhao, X. et al., "A Rapid Bioassay for Single Bacterial Cell Quantitation Using Bioconjugated Nanoparticles," *Proc. Natl. Acad. Sci. USA*, 2004, 101(42):15027-32.
Batich, C. D. et al. "Swelling Behavior of pH-Sensitive Copolymers Based on Styrene and 4-(or 2-) Vinylpyridine" (1993) *Macromolecules*, 26:4675-4680.
Das, C. R. and Su, T. "Particle-Mediated Intravascular Delivery of Oligonucleotides to Tumors: Associated Biology and Lessons From Genotherapy" (2001) *Drug Delivery* 8:191-213.
Dauty, E. et al. "Intracellular Delivery of Nanometric DNA Particles Via the Folate Receptor" (2002) *Bioconjugate Chem*. 13:831-839.
Gabizon, A. et al. "Targeting Folate Receptor With Folate Linked to Extremities of Poly(ethylene glycol)-Grafted Lipsomes: In Vitro Studies" (1999) *Bioconjugate Chem*. 10:289-298.

(Continued)

*Primary Examiner*—Long V. Le
*Assistant Examiner*—Jacob Cheu
(74) *Attorney, Agent, or Firm*—Saliwanchik, Lloyd & Saliwanchik

(57) ABSTRACT

The present invention concerns novel materials and methods to detect low frequency surface changes utilizing modified microspheres. Upon exposing the surface to the modified microspheres of the subject invention, the microspheres selectively adhere to any targeted surface marker.

12 Claims, 1 Drawing Sheet

OTHER PUBLICATIONS

Kranz, D. M. et al. "Conjugates of Folate and Anti-T-Cell-Receptor Antibodies Specifically Target Folate-Recpetor-Positive Tumor Cells for Lysis" (1995) *Immunology*, 92:9057-9061.

Leamon, C. P. and Low, P. S. "Delivery of Macromolecules Into Living Cells: A Method That Exploits Folate Receptor Endocytosis" (1991) *Cell Biology*, 88:5572-5576.

Leckey, A. R. "Active Microspheres for Use in the Treatment of Hepatic Tumors" Master's Thesis, University of Florida (1997).

Lu, Y. and Low P. S. "Folate-Mediated Delivery of Macromolecular Anticancer Therapeutic Agents" (2002) *Advanced Drug Delivery Reviews*, 54:675-693.

Reddy, J. A. et al. "Optimization of Folate-Conjugated Lipsomal Vectors for Folate Receptor-Mediated Gene Therapy" (1999) *Journal of Pharmaceutical Sciences*, 88(11):1112-1118.

Shukla, S. et al. "Synthesis and Biological Evaluation of Folate Receptor-Targeted Boronated PAMAM Dendrimers as Potential Agents for Neutron Capture Therapy" (2003) *Bioconjugate Chem.*, 14:158-167.

Wang, S. and Low, P. S. "Folate-Mediated Targeting of Antineoplastic Drugs, Imaging Agents and Nucleic Acids to Cancer Cells" (1998) *Journal of Controlled Release*, 53:39-48.

Ward, C. M. et al. "Modification of pLL/DNA Complexes With a Multivalent Hydrophilic Polymer Permits Folate-Mediated Targeting In Vitro and Prolonged Plasma Circulation In Vivo" (2002) *The Journal of Gene Medicine*, 4:536-547.

Zhang, Y. et al. "Surface Modification of Superparamagnetic Magnetite Nanoparticles and Their Intracellular Uptake" (2002) *Biomaterials*, 23:1553-1561.

* cited by examiner

MICROPARTICLE-BASED DIAGNOSTIC METHODS

CROSS-REFERENCE TO RELATED APPLICATION

This application claims the benefit of provisional patent application Ser. No. 60/532,167, filed Dec. 23, 2003, which is hereby incorporated by reference in its entirety.

FIELD OF THE INVENTION

The present invention relates to methods for detecting evidence of modifications on surfaces. In a specific embodiment, the subject invention provides diagnostic methods for disease.

BACKGROUND OF THE INVENTION

Low frequency changes on the surfaces of substrates are possible indications of contamination and/or abnormalities. Examples include lead in painted surfaces; scaling inside pipes; mold on carpeting, walls, or heating and cooling ducts; bacteria on skin; and cancer cell receptors. Without early detection and subsequent remediation, these surface modifications can lead to deleterious health, economic, environmental, and structural damage. An area wherein surface modification detection is particularly needed involves the early diagnosis of certain cancers.

A serious global health issue concerns oral cancer and its lack of early detection. Head and neck squamous cell carcinoma (HNSCC) makes up about 4% of all newly diagnosed cancers in the U.S. (30,000 new cases per year), with secondary primary tumors developing at a rate of 2-3% new cases per year (Tabor et al., "Multiple Head and Neck Tumors Frequently Originate from a Single Preneoplastic Lesion" *Amer. J. Path.*, 161 (3) 1051-1060 (2002). In fact, long term survival rates have not improved significantly in the last 20 years. A major preventable cause is thought to be tobacco use; especially the use of chewing tobacco. In some Asian countries, this tobacco use is combined with chewing of betal leaves, and oral cancer rises to 40% of new cancers (Pande et al., "Prognostic Factors in Betel and Tobacco Related Oral Cancer", *Oral Onocology,* 38, 491-499 (2002).

Early detection is hampered because pain and other symptoms are normally not present during early stages. Accordingly, diagnosis usually occurs at a late stage, such as after the primary tumor has metastasized and presented with a lump in the neck. Such advanced cases have a very bad prognosis that is worse than that of breast or prostate cancer (Canto, M. et al., "Views of Oral Cancer Prevention and Early Detection: Maryland Physicians," *Oral Onc.* 38, 373-377 (2002)).

In addition, successful treatment of HNSCC frequently involves radiation therapy and leaves the patient with significant deficits in quality of life factors including decreased saliva production. Surgical removal of deeper lesions, which result from invasion initiated at the surface, also can be very traumatic (e.g., removal of large parts of the tongue or jaw). Early detection allows less invasive treatment, a more positive effect on survival, and a decreased risk of physical dysfunction. Unfortunately, no effective and easily administered screening test is currently available.

Currently, early detection is difficult since early lesions are small, requiring a careful physical examination to detect. For instance, careful examination requires grasping the tongue with gauze, distracting it to a contralateral position, and withdrawing it as far as possible from the oral cavity. Lighting is difficult, since head mirrors, lamps and penlights lack sufficient intensity and color balance to detect the most common pre-cancerous lesions (Mashberg, S. et al., "Early Diagnosis of Asymptomatic Oral and Oropharyngeal Squamous Cancers," CA Cancer J. Clin. 45, 328-51 (1995)). A recent survey of Maryland physicians found that 82% did not routinely do an oral examination, and many felt (incorrectly) that the disease was rare. Some expressed surprise that it was more common than cervical cancer, where screening was routinely done, but expressed the view that a continuing education class in detecting oral cancer would draw little interest (Canto, M. et al., "Views of Oral Cancer Prevention and Early Detection: Maryland Physicians," *Oral Onc.* 38, 373-377 (2002). An easy to use, accurate screening test to detect oral cancers in the early onset of the disease would be highly beneficial.

Toluidine blue dye has been used to aid in the detection of oral cancer because it is a vital stain that colors various lesions for easier visibility during oral examinations (Mashberg, S. et al. "Early Diagnosis of Asymptomatic Oral and Oropharyngeal Squamous Cancers," CA Cancer J. Clin. 45, 328-51 (1995)). However, toluidine also stains non-malignant lesions, such as ulcers, requiring additional examination after a period of time sufficient for healing to take place. In addition, the use of toluidine to stain lesions requires direct observation by a health care professional.

Certain molecules are known as indicators for cancerous growths. For example, cell surface receptors for the vitamin folic acid are overexpressed on most human cancer cells, including those of the mucosa (Wang S, Low P S., "Folate-Mediated Targeting of Antineoplastic Drugs, Imaging Agents, and Nucleic Acids to Cancer Cells" *J. Control Release* 1998 Apr. 30, 53 (1-3): 39-48) and other epithelial malignancies of the head and neck (Lu, Y and Low, P., "Folate-Mediated Delivery of Macromolecular Anticancer Therapeutic Agents," *Advanced Drug Delivery Reviews* 54, 675-693 (2002). Additional surface receptors with known overexpression in HNSCC are those for transferrin (TF), epidermal growth factor (EGF) and vascular endothelial growth factor (VEGF).

The folic acid molecule has three fragments chemically linked: 6-methylpteridin, p-amino benzoic acid (PABA), and glutamic acid. Naturally occurring folic acid can have up to eight glutamic acid residues linked together through the carboxylate group on the amino acid's side chain.

Folate is needed in the synthesis of DNA nucleotides and the methyl group of thymine. Hence, folate is required in rapidly growing cell populations, and more rapid uptake is required since it cannot be synthesized by the cell. Syntheses of cell-surface receptors for the molecule are upregulated, and the receptors mediate both membrane transport and endocytosis of the free folate and folate conjugates.

Because of this enhanced level of folate receptor on the cell surface, attachment of folate to genes, contrast agents, liposomes, drugs, dyes and other markers has been frequently used to specifically target cancer cells in the presence of large amounts of normal tissue (Wang S, Low P S., "Folate-Mediated Targeting of Antineoplastic Drugs, Imaging Agents, and Nucleic Acids to Cancer Cells" *J. Control Release* 1998 Apr. 30, 53 (1-3): 39-48); Lu, Y and Low, P., "Folate-Mediated Delivery of Macromolecular Anticancer Therapeutic Agents," *Advanced Drug Delivery Reviews* 54, 675-693 (2002); Reddy J A, Dean D, Kennedy M D, Low P S "Optimization of Folate-Conjugated Liposomal Vectors for Folate Receptor-Mediated Gene Therapy" *J. Pharm Sci.,* 1999 November; 88 (11): 1112-8; Lu, Y and Low, P., "Folate-Mediated Delivery of Macromolecular Anticancer Therapeutic Agents," *Advanced Drug Delivery Reviews* 54, 675-693

(2002; Das C R, Su T. "Particle-Mediated Intravascular Delivery of Oligonucleotides to Tumors: Associated Biology and Lessons from Genotherapy" *Drug Deliv.* 8 (4): 191-213, 2001). When using folate as a conjugated targeting agent, it was found that the site of folate attachment had to be at the γ-carboxylate group to allow bonding of the other end to the receptors (Leamon, C and Low, P., "Delivery of Macromolecules into Living Cells: A Method that Exploits Folate Receptor Endocytosis" *Proc. Natl. Acad. Sci USA* 88, 5572-5576 (1991). There are at least two types of cell surface receptors for folate (α and β), which both have very high binding affinities (nano molar) and vary in levels with cell type (Kranz D M, Patrick T A, Brigle K E, Spinella M J, Roy E J "Conjugates of Folate and Anti-T-Cell-Receptor Antibodies Specifically Target Folate-Receptor-Positive Tumor Cells for Lysis" *Proc Natl Acad Sci USA* 1995 Sep. 26; 92 (20): 9057-61).

One carrier mechanism for delivering substances to various locations is the microsphere. Microspheres containing surface modifications can be manufactured that are both pH-sensitive and magnetic. Many good methods exist to make microspheres in different size ranges from a wide range of polymers that incorporate useful components such as dyes, drugs or magnetic powders (Karsa, D. and Stephenson, R., "Encapsulation and Controlled Release" *The Royal Society of Chemistry*, Pulisher, Cambridge, UK. 1993; Hafeli, U. et al., ed., "Scientific and Clinical Applications of Magnetic Carriers" *Plenum Press*, NY (1997); Batich, C., Jun, Y., Bucaria, C and Elsabee, M. "Swelling Behavior of pH-Sensitive Copolymers Based on Styrene and 4- (or 2-) Vinylpyridine" *Macromolecules,* 126, pp. 4675-4681 (1993). Surface modification of microspheres for targeting purposes is also a well-established technology, and many types of these particles are available commercially from suppliers such as Bangs Laboratories. Methods of immobilizing folate, in particular, have been developed using di-functional coupling agents (Dauty et al. 2002 July-August; 13 (4): 831-9 Intracellular delivery of nanometric DNA particles via the folate receptor).

Diagnostic applications utilizing microspheres are known (U.S. Pat. Nos. 6,268,222; 6,327,410; 6,417,340 and 6,495,325). Some use color changes as indications for diagnosis; others do not.

U.S. Pat. No. 6,221,579 to Everhart et al., describes a diagnostic system using functionalized microspheres that bind with analytes. The technology of the '579 patent is specifically engineered for in vitro use. A polymer film is purposely adapted to allow light diffraction when the microspheres are bound to the desired analyte.

U.S. Pat. No. 5,919,633 to Tausk et al., describes a diagnostic method utilizing liposomes that change color in the presence of a target antigen. The surface of the liposomes are coated with an antigenic structures that break down the liposome in the presence of the target antigen releasing the color changing marker. The '633 patent pertains to testing taking place outside the body. The diagnostic marker is in the change of color, not in the degree of change.

It is an object of the present invention to provide a method to detect a wide variety of changes on surfaces.

To fill the current void in early diagnostic methods in detecting cancer cells, it is an object of the present invention to provide a method for detecting cancer cells in vivo. It is a further object to provide a method for diagnosing HNSCC in oral mucosa. It is also an object to provide a kit for home or clinical use for diagnosing HNSCC.

BRIEF SUMMARY OF THE INVENTION

The present invention provides materials and methods for evaluating surfaces for low frequency changes. These changes may be caused by, for example, foreign body growth or settlement. Such changes are often accompanied by surface markers that are associated with changes that have occurred, are occurring, or are impending. The subject invention utilizes specifically designed microspheres in a system for easily and accurately detecting these surface changes.

In a particular embodiment of the subject invention, microspheres are modified to comprise species with which a surface marker interacts. The surface suspected of bearing the low-frequency changes (with associated marker(s)) is contacted with the microspheres, and the microspheres adhere to the exposed marker(s), if they are present.

In a specific embodiment, the present invention can be used to detect oral cancer. Oral cancer cells frequently over-express certain receptors, including, for example, the receptor for folic acid. Accordingly, microspheres can be modified with folates attached to, or embedded in, the microsphere surface. These folate-modified microspheres preferentially bind to the cancer cells that over-express receptors for folate.

In a preferred delivery system, the cancer-detecting microspheres of the subject invention are incorporated into a solution for use as mouthwash. When a person rinses the oral cavity with the mouthwash, the folate-modified microspheres adhere preferentially to any cells over-expressing folic acid receptors. Expectorated mouthwash is then collected and analyzed for a decrease in microsphere concentration, which indicates oral cancer.

A further embodiment for the detection of oral cancers comprises an additional rinsing step with a mouthwash containing an ingredient that dislodges the microspheres from the initial mouthwash. After rinsing the oral cavity pursuant to this additional rinsing step, the expectorated mouthwash from this embodiment is collected and analyzed for any dislodged folate modified microspheres. Advantageously, the two washes can be modified to contain two distinct visual indicators, preferably dyes, that are released upon proper stimulation. If the color of the solution matches the visual indicator incorporated into the set of microspheres with the folate-modified surface, the color change indicates a likelihood of oral cancer.

Another aspect of the present invention provides a composition of microspheres in a carrier that are utilized in the method of the present invention. The microspheres can comprise polymers and monomers of methyl methacrylate and N,N-diethylaminoethyl methacrylate. The carrier can be selected for its compatibility with the surface to be tested, and examples include, without limitation, aqueous solutions, organic solvents, powders, aqueous lotions, petroleum lotions, glosses, and films. Advantageously, these microspheres can be further modified to include detectable compounds (such as visual indicators), drugs, flavorings, sweeteners, antiseptic agents, and/or compounds to aid in collection. In one embodiment, multiple sets of microspheres are envisaged, so that ratios between markers (e.g, dyes) can indicate the extent of disease or type of disease.

An additional aspect of the present invention provides a kit for an easy to use, inexpensive home or clinical test for the detection of oral cancers. In one embodiment the kit includes a first vial containing a mouthwash, wherein the mouthwash comprises at least one set of microspheres, wherein one set of microspheres are modified with a species to which an oral cancer marker interacts, wherein any remaining sets of microspheres are not modified with the species; a second vial of mouthwash, wherein the pH of the mouthwash is about 5.5; and a container for collecting expectorated mouthwash from the second vial. The kit can optionally contain at least one swab or sponge attached to a holder, wherein one swab can be used to wipe an oral mucosal surface with the mouthwash of the first vial, and/or another swab can be used to wipe an oral mucosal surface with the mouthwash of the second vial.

DETAILED DESCRIPTION OF THE INVENTION

Figure 1:
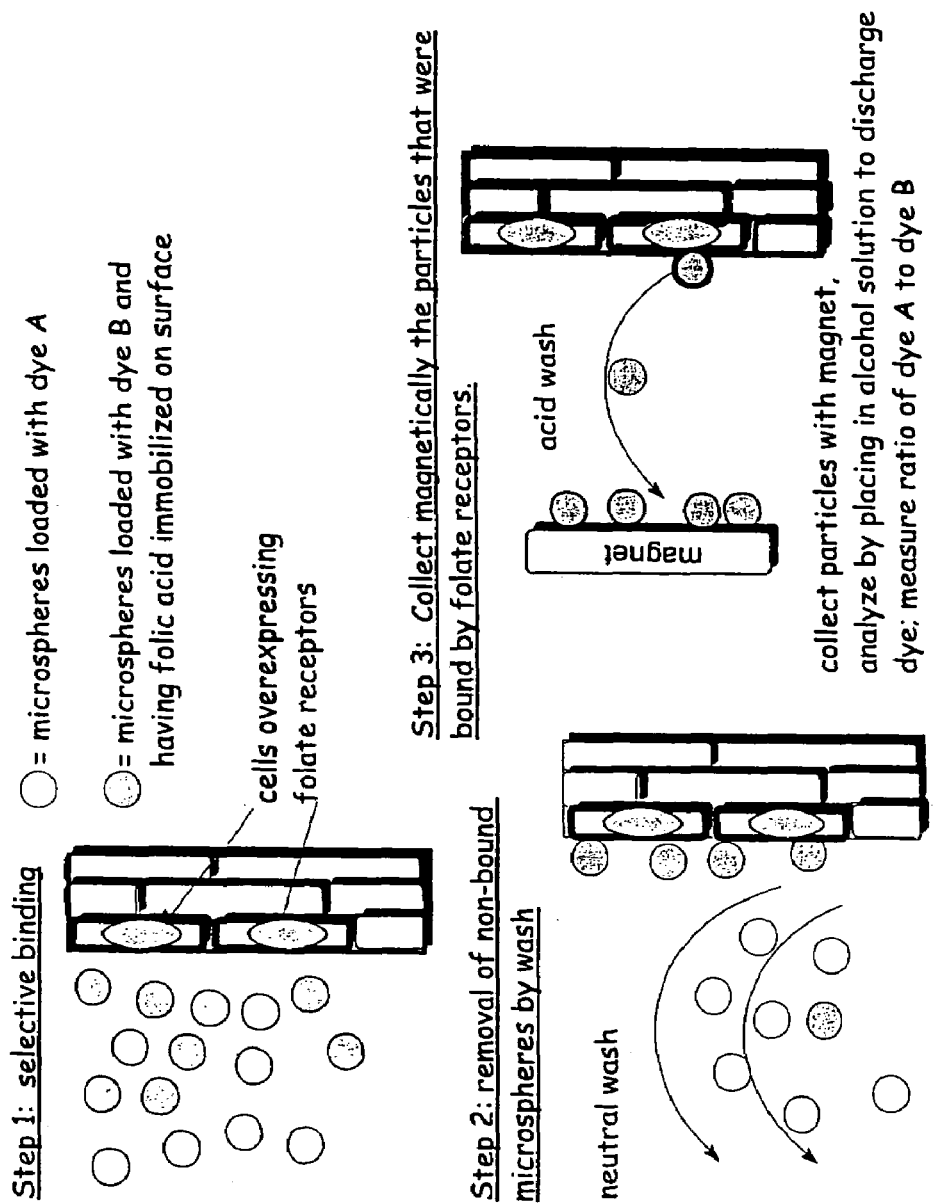
FIG. 1 shows a schematic for the process of selective binding of modified micro spheres.

Low-frequency surface changes are possible indications of surface growth, settlement and/or contamination. Such surface changes are often the first steps to occur in processes that then progress to cause deeper, bulk changes such as tissue invasion or metastasis. Although visual identification and/or verification of such surface alterations may be possible after an extended period of time, the present invention provides a methods for early detection of minute surface changes. Early detection can be used to, for example, minimize any subsequent adverse consequences of the changes.

In a preferred embodiment, the method of the present invention involves detecting low frequency surface changes by exposure to modified microspheres. Preferably, the method provided by the present invention comprises contacting the microspheres with a surface suspected of low-frequency change, collecting any microspheres that do not adhere to the surface, and analyzing the non-adhering microspheres for a decrease in concentration or quantity of the modified microsphere or for a visual indicator. A method of the subject invention is shown in FIG. 1.

In accordance with the present invention, many surface changes (and their associated markers) are detectable including, but not limited to, metals (e.g., lead in painted surfaces; scaling in pipes), organisms (e.g., mold on carpeting, walls, or heating and cooling ducts; algae on pipes; bacteria on skin or similar surfaces) and disease indicators (e.g., a cancer cell's increased receptor activity for folic acid, TF, EGF, or VEGF). In specific embodiments, the present invention is used detect disease at an early stage. For example, the present invention can be used to detect cancer cells on mucosal surfaces.

One composition of the present invention utilizes microspheres modified to detect low frequency surface changes. As used herein the term "microspheres" is understood to include microbeads, microparticles, and microcapsules and also the corresponding name-equivalents. In one embodiment, the microspheres comprise materials that swell when the pH of their environment changes.

In a particular embodiment of the subject invention, microspheres are modified to comprise species with which a surface marker interacts. The surface suspected of bearing the low-frequency changes (with associated markers) is contacted with the microspheres, and the microspheres adhere to the exposed marker.

Advantageously, the composition can be specially synthesized to target specific surface markers in particular applications. If the microsphere is expected to come into contact with humans or animals, the indicator and all of the components can be FDA approved to limit harmful interactions with the end user.

In one embodiment, for microspheres utilized for detecting oral cancers, the microspheres are incorporated into an aqueous liquid suspension. Furthermore, the suspension can be designed to minimize settling of the heavier particles. Preferably, less than 25% of the microspheres significantly settle thirty seconds after stirring.

One embodiment of the present invention comprises exposing a surface to a mixture of two or more types of microspheres simultaneously. Each type of microspheres has a distinct characteristic so that it will either adhere or not adhere to the surface marker being sought. The microspheres can then be collected in two stages, so that one stage collects only (or predominantly) one set of microspheres (such as the weakly adhering set), and a second collection collects the remaining set. A subsequent evaluation step identifies the relative amounts of microspheres collected in each step and indicates the relative amount of specific surface markers present. This two step embodiment provides a great increase in sensitivity over methods involving depletion, because much background is removed.

Detection of Oral Cancer

For detecting oral cancer, folic acid or iron-containing transferrin (TF) (or other specie that interacts with a cancer marker) can be attached to the microsphere. Cancer cells generally overexpress receptors for these molecules. Accordingly, the microspheres will preferentially bind to cancer cells.

A first set of microspheres can incorporate a visual indicator. Preferably, the visual indicator is a dye. More preferably, the visual indicator is food coloring. In one preferred embodiment, folic acid is immobilized on the surface of the first set of microspheres. In a specific embodiment, a second set of microspheres is identical to the first except that the second set's surface is not modified with folic acid, and it contains a different visual indicator, for example, a red food coloring dye. In a preferred embodiment, both sets of microspheres incorporate a species to ease collection. Preferably, that species is iron oxide. More preferably, that species is magnetite.

In accordance with this embodiment of the present invention, a patient rinses the oral cavity with the mouthwash containing the first set of microspheres and collects the expectorated mouthwash for analysis. Contacting the mouthwash with the mucosal surface preferentially binds the folate modified microspheres to any cancer cells. If many cancer cells are present, collection of the expectorated mouthwash would be expected to be prominently or completely depleted of the folate modified microspheres. The expectorated mouthwash is analyzed to measure the decrease in concentration of folate modified microspheres.

However, if the number of modified microspheres remaining in the expectorated mouthwash were small, the microsphere concentration could be hard to detect or require specialized analytical equipment. Advantageously, a further embodiment utilizes visual indicators for easy to see indications of oral cancers. It incorporates a second mouthwash that is designed to dislodge the folate-bound microspheres. The second mouthwash can comprise, for example, a second set of microspheres without a folate modified surface but with an incorporated visual indicator, for example, a colored dye.

For dislodgement of the first set of microspheres from the surface of the oral cavity, one embodiment utilizes a slightly acidic pH solution for dislodgement; another embodiment utilizes a free folic acid.

Following rinsing the oral cavity with the second mouthwash (e.g., acidic solution with no microspheres), the second expectorated mouthwash contains any of the first set of microspheres that were bound to the folate receptors without interfering (folate-free) micro spheres.

To determine if any microspheres from the labeled set are present, the microspheres are concentrated. Preferably, a permanent magnet concentrates the microspheres by attracting the magnetite in the microspheres. Visual verification of the cancer cells is accomplished by releasing the visual indicator, preferably dye, encapsulated within the microsphere. Dye release is stimulated, in one embodiment, with solvent. Advantageously, equilibrium for dye release takes place in less than hour. In another embodiment, dye release is stimulated with a change in pH. Released dye is easily detected visually, and a color matching the dye from the first set of microspheres indicates likely oral cancer. A comparison color chart made from mixtures of the two dyes at various levels can aid in analysis. A more sensitive analysis of the color concentration can be made with a simple spectrophotometer.

Microspheres

The microspheres utilized according to the present invention can be manufactured with techniques known in the art. Accordingly, the microspheres can be synthesized using, for example, suspension polymerization, dispersion polymerization, and/or seeded polymerization. The selection of the polymerization method can be used to control the particle size of the individual microsphere. In a preferred embodiment, the particle size of the microsphere is large enough to be easily captured by a magnet, yet small enough not to be easily discharged from the target surface. Preferably, the particle size of the microsphere is within the range of about 1 to about 400 µm. More preferably, the particle size is about 4 to about 50 µm. Most preferably, the particle size is about 4.5 to about 5.5 µm.

In a specific embodiment, methyl methacrylate microspheres can be produced using a suspension polymerization method, yielding a broad particle size distribution with ranges centered from about 1 to 400 µm. Smaller microspheres (single µm size) with a narrower size distribution can be made via dispersion polymerization. Yet smaller (submicron sized) microspheres can be produced via emulsion polymerization. Acrylate based microspheres can also been produced using seeded polymerization mechanisms to yield a variety of monodisperse size ranges. PH-sensitive microspheres, with activation pH typically around 5.5, but adjustable above or below that value, can also be formulated (Batich, et al., "Swelling Behavior of pH-Sensitive Copolymers Based on Styrene and 4- (or -2) Vinylpyridine," Macromolecules, 126, 4675-4681 (1993)).

In one embodiment, the microspheres comprise methyl methacrylate, N,N-diethylaminoethyl methacrylate, and/or polymers of each, and a species to which a surface marker preferentially binds or otherwise detectably interacts. Preferably, when the surface change is head and neck squamous cell carcinoma (HNSCC), the species that will bind to an associated marker is selected from the group consisting of folates, TF, EGF, and VEGF. The species can be, for example, attached to the surface of the microsphere or embedded within.

For microspheres comprising polymethylmethacrylate (PMMA), an active functional group can first be formed on the microsphere by either hydrolysis or aminolysis. For example, first the microspheres can be immersed in a dilute (1 N) solution of ethylene diamine in hexane. The ester bonds on the surface can react with the amino group and form amide bonds with a free primary amino group. Folic acid can be reacted with dicyclohexyl carbodiimide, and the solution added to amino derivatized microspheres.

To aid in surface attachment, a spacer species can be attached to the microsphere by reaction with the microsphere surface. Preferably, the spacer species is a difunctional polyethylene glycol (PEG). More preferably, the spacer species is a t-BOC protected $NH_2$-PEG. Advantageously, t-BOC protected $NH_2$-PEG has one free amino group to react with folate in DMSO solvent. After deprotection with trifluoroacetic acid, the reagent can be reacted directly with the methacrylate surface. In a specific embodiment, a PEG800 is useful as a linker. (Gabizon et al., "Targeting Folate Receptor with Folate Linked to Extremities of PEG-grafted Liposomes: in vitro Studies" *Bioconjugate Chem.* 10, 289-98 (1999)). Alternatively, other difunctional PEG's can be attached as a spacer to folate and have been used to target boron-containing molecules (for boron neutron capture therapy, i.e., BNCT) to the folate receptor expressed on human KB cancer cells (ATCC #CCL 17), a line derived from an epidermal carcinoma of the oral cavity. (Shukla, et al., "Synthesis and Biological Evaluation of Folate Receptor-Targeted Boronated PAMM Dendrimers as Potential Agents for Neutron Capture Therapy" *Bioconjugate Chem.*, 14, 158-167 (2003)).

Microsphere Loading

The microspheres utilized according to the present invention can comprise a visual indicator encapsulated within the microsphere. Optionally, the visual indicator can be incorporated as a nanoparticle within the microsphere. Preferably, the visual indicator is a dye. More preferably, the visual indicator is a food colorant. Under proper stimulation, the microsphere releases the visual indicator. A pH change or a solvent change are typical stimulants.

The method of loading visual indicators into the subject microspheres can comprise a multi-step process. In one embodiment, dried microspheres are first washed in methanol and then permitted to air dry. Washed microspheres are immersed in a 10 wt % solution of dye in alcohol (usually ethanol or methanol) for 24 hours, removed from solvent liquid, and the alcohol permitted to evaporate. The microspheres are then repeatedly washed in fresh water, collected by centrifugation, and finally dried in a vacuum oven at 60° C. under a modest vacuum of about 100 Torr. Solvents for the swelling can be chosen based on the solubility parameters of the solvents and the polymers. Mixed solvents can also be used to maintain the use of materials generally recognized as safe for human exposure in small quantities:

PMMA: $\delta=9.5$ $(cal/cm^3)^{1/2}$
Isopropanol: $\delta=8.8$ $(cal/cm^3)^{1/2}$
Water: $\delta=23.4$ $(cal/cm^3)^{1/2}$ To match the solubility parameter of the polymer almost exactly, a 95 v/v % isopropanol and 5 v/v % water solution will yield $\delta=9.5$ $(cal/cm^3)^{1/2}$, as determined by a rule of mixtures calculation. Adjustment of the solvent composition will allow swelling, but not dissolution. Preferable dyes include 9-amino acridine and fluorescein. Other dyes can also be used including, for example, indigostine, quinoline yellow, red 2 g, and mixture thereofs.

In the case of microspheres to be used for cancer cell detection, a mix of folate surface-labeled particles can be loaded with dye "B" and can be mixed with an equal amount of microspheres without surface folate, but containing dye "A." If there is no selective binding, then collected microspheres will show equal amounts of dye "A" and dye "B." If folate binding is occurring, then recovery of the bound microspheres (after rinsing off unbound ones) show an excess of dye "B" relative to dye "A." This difference can be determined by, for example, visual inspection, optionally with comparison to a color chart, or with an analysis by a spectrophotometer.

Formulations and Uses

The microsphere composition of the present invention can be transported by varying the delivery system in which the composition contacts any location. Examples of delivery systems include, but are not limited to, aqueous solutions, for example, mouthwashes; organic solvents; powders; aqueous or petroleum based lotions; and glosses or films.

The composition can further comprise flavoring to improve taste. Optionally, the flavoring can be incorporated into the microsphere or added to the delivery system.

Advantageously, in one embodiment the present invention provides an easy to use beneficial screening test for oral cancer that can be administered by physicians and other health care professionals or less highly trained laypersons. Another aspect of the invention involves a kit for administering a simple, possibly home-based test for likelihood of oral cancer.

The system of the subject invention can also be used as a vehicle for the in situ delivery of biologically active agents. The biologically active agents incorporated into, or included as an additive within, the microspheres of the subject invention can include, without limitation, medicaments, vitamins, mineral supplements, substances used for the treatment, prevention, diagnosis, cure or mitigation of disease or illness, substances which affect the structure or function of the body, or drugs. The active agents include, but are not limited to, antifungal agents, antibacterial agents, anti-viral agents, antiparasitic agents, growth factors, factors affecting angiogenesis, anesthetics, mucopolysaccharides, metals, cells, and other wound healing agents.

As used herein, the term "adhere" refers to substantial attachment or binding of the microparticle species to a surface marker.

As used herein, the term "fresh composition" refers to an unused mouthwash composition. The composition contains a plurality of microspheres, wherein each microsphere has a species optionally embedded within the surface of the microparticle or attached to the surface of the microparticle, and the species is selected for its interaction with a target surface marker.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting.

EXAMPLE 1

Home Test Kit

One embodiment of the present invention involves a kit for a home based test for oral cancer. Optionally, the kit can be administered in a clinical setting such as a physician's or a dentist's office. The kit contains two marked vials each holding a mouthwash—one mouthwash with the first set of folate-modified and unmodified microspheres and one mouthwash with the just an acidic solution—and an empty collection container. The accompanying directions instruct the consumer or test administrator to rinse the oral cavity with the mouthwash containing the first set of microspheres for a sufficient amount of time to ensure complete contact between the mucosal surface and the mouthwash followed by disposal of the expectorated mouthwash. Subsequently, the mucosa should be exposed to the second mouthwash, and the resulting expectorate stored in the collection container and sealed. The collection container can then be submitted to a qualified laboratory for analysis of the expectorate for the colored dye indicators. Alternatively, particles can be concentrated with a magnet and the supernatant liquid discarded. A final vial containing a releasing solvent can be added to these particles, and the color compared against a standard chart for immediate interpretations.

EXAMPLE 2

Method of Use

Microspheres prepared in accordance with the subject invention can be incorporated into a liquid suspension, which can be used as a, for example, a mouthwash delivery system for oral mucosa. Preferably, the properties of this suspension include the ability to prevent significant settling of the heavier particles (less that 25%) over 30 seconds after stirring, but the compositions can simply use microspheres in pH 7.4 phosphate buffered saline (PBS) or culture media.

In one example, a few cubic millimeters of biopsy tissue is placed in a polyethylene 5 mL centrifuge tube, containing PBS, and a mixture of the two microsphere populations (folate surface with dye "A" and non-folate surface with dye "B"). The tubes are gently shaken for one minute in an automated shaker, and then removed for extraction of microspheres by filtering the PBS mixture through filters with porosity greater than 100 micrometers, or simply removing the tissue with forceps. This removes any non-bonded microspheres. The tissue is examined with optical microscopy since the two types of microspheres can also be distinguished visually. The image is captured in a morphometric image analysis system (Zeiss Axioplan 2 Imaging System and microscope), and the relative amounts of the two particles measured by counting (grid reticle on a representative field) or processing with the software.

EXAMPLE 3

Attachment of Folic Acid

Folic acid can be attached to the surface of the microspheres by means of a technique described by Zhang et al. (Zhang, Y, N. Kohler, & M. Zhang "Surface modification of superparamagnetic magnetite nanoparticles and their intracellular uptake." *Biomaterials,* 2002 April; 23 (7): 1553-61.) The mechanism for attachment of folic acid onto microspheres is shown in Scheme A.

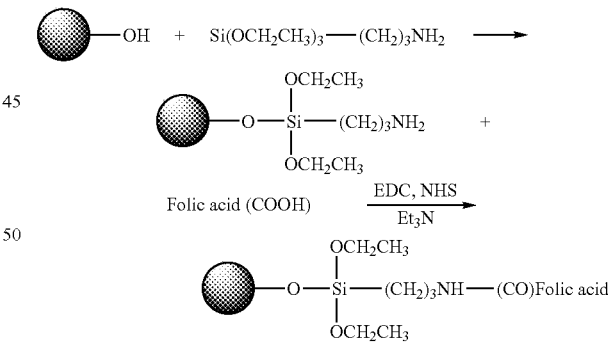

Dried particles are dispersed in 3 mM (3-aminopropyl)-trimethoxysilane in 5 ml toluene, vortexed and sonicated, then incubated at 60° C. for 4 hours. The product is centrifuged, and the precipitate is placed in hexane and sonicated for 10 minutes, then washed with hexane and ethanol. A solution is made of 1.5 ml each of 15 mM NHS (N-hydroxy succinimide) and 75 mM EDC (1-ethyl-3-(3-dimethylaminopropyl) carbodiimide) and 1 ml 10 mM folic acid in DMSO, to which the precipitate is added, and ethylene triamine used as a catalyst. The pH is adjusted to 9 and the mixture incubated at 37° C. for 4 hours, after which the precipitate is centrifuged off and washed with de-ionized water, then vacuum dried overnight.

EXAMPLE 4

Magnetic Microspheres

A variety of magnetically responsive microspheres can be made by means of seeded polymerizations, as well as by means of a post-polymerization in situ precipitation of a magnetic iron oxide. The iron oxide can be superparamagnetic magnetite, imparting magnetic responsiveness without remnant magnetization of the particles. This is confirmed by the combination of magnetic responsiveness, permitting magnetic separation of the microspheres, and absence of agglomeration or coagulation tendencies, which would occur if there was remnant magnetization.

Superparamagnetism is a function of the crystal size of the iron oxide particles (<30 µm), (as formed by base catalyzed precipitation of ferric and ferrous iron compounds) and is desirable for the formation of the aqueous suspension mouth wash.

The magnetite can be made beforehand in this superparamagnetic size range, and dispersed in monomer by coating with oleate. This process can yield a microsphere population with polymer on the surface instead of magnetite. The surface can then be hydrolyzed with strong base (1N NaOH for 5 minutes) to produce free acid groups on just the surface (Batich et al. (1993) "Swelling Behavior of pH-Sensitive Copolymers Based on Styrene and 4- (or -2) Vinylpyridine," *Macromolecules* 126: 4675-4681), and can provide a site for folate attachment. Acrylate based microspheres can be prepared by using seeded dispersion polymerization in a variety of sizes.

As per Noguchi et al. (1993) "Preparation and Characterization by Thermal Analysis of Magnetic Latex Particles" *Journal of Applied Polymer Science* 48: 1539-1547, one can perform an emulsifier-free emulsion polymerization in the presence of a ferrofluid (composed of a magnetite colloidal suspension), which yields submicron through micron sized PMMA particles with a high degree of incorporated iron oxide (up to 20% range). Polymerization is carried out with MMA monomer and ferrofluid at 70° C. for 20 hours in sealed glass vials. A seeded polymerization, using the products of the emulsion polymerization as a core, could also be carried out to increase the size of the particles produced. (Leckey, A., "Active Microspheres for the Treatment of Hepatic Tumors" Master's Thesis, University of Florida (1997)). Monomers are combined in the appropriate ratios and include initiator (3 wt/vol % AIBN (2,2'-azobisisobutyronitrile)). 5 vol % monomer phase is added to the dispersion sovent, typically an 80/20 mix of absolute ethanol and DI (de-ionized) water, with 0.6 wt/vol % stabilizer (PVP40—poly (vinyl pyrrolidone)). The polymerization mixture is nitrogen purged for 2 minutes and polymerized within 40 ml screw top glass vials, in a shaking water bath set to 100 cpm and 70° C. for 24 h.

Subsequently the product is diluted 2:1 with water and stirred or sonicated for 30 minutes, then washed by repeated centrifugation, decantation of supernatant and re-suspension in DI water. As per the procedure of Leckey (1997), nitrogen purged monomer solution of the desired composition (including initiator) is introduced into hot (70° C.) stabilizer solution (ionic and polymeric stabilizers) under rapid stirring (~900 rpm). After monomer addition, the solution temperature is ramped up to 85° C. and held for 4 hours. After cooling to room temperature, the solution is decanted into water, and the microspheres produced are cleansed by repeated centrifugation/decantation and re-suspension. The procedure utilized is based on those detailed by Lea et al. (Lea T et al. "Monosized, magnetic polymer particles: their use in separation of cells and subcellular components, and in the study of lymphocyte function in vitro." *J Mol Recognit*. 1988 February; 1 (1): 9-18. Review.) 2 ml each of 0.055 M ferrous chloride tetrahydrate and 0.096 M ferric chloride hexahydrate are mixed by stirring or sonication for 30 minutes. 1 ml ammonium hydroxide solution (28%) is added to induce pH driven precipitation of iron oxide, and mixing is continued for 15 min, after which the product is collected by centrifugation and decantation, followed by repeated magnetic separation and washing cycles. The superparamagnetic character of the precipitate is confirmed by the fact that the particles do not agglomerate independently.

It should be understood that the examples and embodiments described herein are for illustrative purposes only and that various modifications or changes in light thereof will be suggested to persons skilled in the art and are to be included within the spirit and purview of this application.

I claim:

1. A method for detecting the presence of a marker associated with oral cancer on an oral cavity mucosal surface wherein said method comprises:
    a) contacting the oral cavity of a patient with a composition, wherein the composition comprises at least one set of microparticles and a carrier, wherein the microparticles comprises a specie that is capable of adhering to the oral cavity mucosal surface marker; and
    b) determining whether any microparticles have adhered to the surface marker, wherein adherence of the microparticles to the surface indicates the presence of the marker, wherein the determining step comprises either or both of the following:
        i) recovering the composition from the surface and determining whether the contacting of the composition with the surface reduced the concentration of microparticles in the composition; and
        ii) dislodging any microparticles that adhere to the surface with a second composition, and analyzing the second composition to determine if any microparticles are present, wherein the presence of microparticles indicates the presence of the marker;
    wherein the specie is selected from the group consisting of folic acid, folate, and a folate conjugate; and wherein the carrier is a neutral mouthwash aqueous solution.

2. The method according to claim 1, wherein the dislodging step comprises contacting the surface with an acidic solution.

3. The method according to claim 1, wherein the microparticles further comprise a visual indicator; and wherein the method further comprises releasing the visual indicator to facilitate detection of the microparticles.

4. The method according to claim 1, wherein the specie is attached to the surface of the microparticle or is embedded within the surface of the microparticle.

5. The method according to claim 1, wherein the specie is attached to the surface of the microparticle via a spacer.

6. The method according to claim 5, wherein the spacer is a difunctional polyethylene glycol.

7. The method according to claim 1, wherein the size of the microparticle is within the range of about 1 µm to about 400 µm.

8. The method according to claim 1, wherein the microparticle further comprises a concentrating agent, a visual indicator, or a biologically active agent.

9. The method according to claim 8, wherein the visual indicator is encapsulated with the microparticle and is released by a change in pH or a change in solvent.

10. The method according to claim 8, wherein the concentrating agent is iron oxide or magnetite.

11. The method according to claim 1, wherein the dislodging step comprises contacting the surface with a free folic acid solution.

12. The method, according to claim 1, wherein the aqueous solution has a pH of about 7.4.

* * * * *